(12) United States Patent
Muntermann

(10) Patent No.: US 9,095,696 B2
(45) Date of Patent: Aug. 4, 2015

(54) APPARATUS FOR MAGNETIC FIELD THERAPY

(76) Inventor: Axel Muntermann, Wetzlar-Nauborn (DE)

( * ) Notice: Subject to any disclaimer, the term of this patent is extended or adjusted under 35 U.S.C. 154(b) by 962 days.

(21) Appl. No.: 13/000,890

(22) PCT Filed: Jun. 23, 2009

(86) PCT No.: PCT/EP2009/004509
§ 371 (c)(1),
(2), (4) Date: Jan. 20, 2011

(87) PCT Pub. No.: WO2009/156117
PCT Pub. Date: Dec. 30, 2009

(65) Prior Publication Data
US 2011/0118535 A1     May 19, 2011

(30) Foreign Application Priority Data
Jun. 23, 2008 (DE) .......................... 10 2008 029 415

(51) Int. Cl.
*A61N 1/00* (2006.01)
*A61N 2/02* (2006.01)
*A61N 2/06* (2006.01)

(52) U.S. Cl.
CPC .... *A61N 2/02* (2013.01); *A61N 2/06* (2013.01)

(58) Field of Classification Search
CPC .................................. A61N 2/06; A61N 2/02
USPC .................................. 600/9–15; 128/897–899
See application file for complete search history.

(56) References Cited

U.S. PATENT DOCUMENTS

| 6,558,311 | B1* | 5/2003 | Muntermann | 600/13 |
| 2003/0069464 | A1 | 4/2003 | Muntermann | |
| 2007/0287908 | A1* | 12/2007 | Karl et al. | 600/415 |
| 2008/0139871 | A1* | 6/2008 | Muntermann | 600/13 |
| 2008/0211498 | A1* | 9/2008 | Dannels et al. | 324/309 |

FOREIGN PATENT DOCUMENTS

| CN | 1929889 | 3/2007 |
| DE | 26 10 589 | 9/1977 |
| DE | 91 11 936 | 11/1991 |
| DE | 198 27 736 | 12/1999 |
| EP | 0 228 537 | 7/1987 |
| EP | WO 99/66986 | 12/1999 |
| WO | 2005/075019 | 8/2005 |
| WO | 2006/024602 | 3/2006 |
| WO | 2008/073512 | 6/2008 |

\* cited by examiner

*Primary Examiner* — Christine H Matthews
*Assistant Examiner* — Sunita Reddy
(74) *Attorney, Agent, or Firm* — Pearl Cohen Zedek Latzer Baratz LLP

(57) ABSTRACT

The invention relates to a device for magnetic field therapy which is preferably adapted for producing nuclear magnetic resonances in the tissue to be treated. The device comprises a base and two side parts having coils integrated therein.

14 Claims, 6 Drawing Sheets

APPARATUS FOR MAGNETIC FIELD THERAPY

This application is a U.S. national stage of PCT/EP2009/004509 filed Jun. 23, 2009 which claims priority to and the benefit of German Application No. 10 2008 029 415.2 filed on Jun. 23, 2008, the contents of which are incorporated herein by reference.

FIELD OF THE INVENTION

The invention relates to a device for magnetic field therapy.

BACKGROUND OF THE INVENTION

Methods for magnetic field therapy and associated devices for performing same are known.

A method for magnetic field therapy in which the therapeutic effect relies on the effect of nuclear magnetic resonance is described in European patent document EP 1 089 792 B1 (patent holder Axel Muntermann).

This method uses a device in which a substantially static magnetic field is superimposed by an alternating magnetic field perpendicular thereto.

A requirement for achieving nuclear magnetic resonance is that at least the static magnetic field in the treatment zone has a field strength as homogenous as possible, since otherwise nuclear magnetic resonance only occurs in a part of the treatment zone.

In practice, for generating alternating magnetic fields a Helmholtz coil is used, for example, i.e. an arrangement of two annular or cylindrical coils spaced from each other.

A disadvantage of such a coil arrangement or an annular coil in general is that the patient has to lie down in the coil during treatment. This is not comfortable, in particular for older or adipose persons. Moreover, the annular arrangement extending around the patient may cause claustrophobia.

When treating animals the handling of an annular coil is also impractical, since the animal has to be driven in, e.g. on a carriage, and so would have to be fixed in many cases, or since the air coil required for treatment has to be slid onto the joint to be treated or the area to be treated.

OBJECT OF THE INVENTION

An object of the invention, therefore, is to at least mitigate the shortcomings of the prior art mentioned above.

In particular, an object of the invention is to provide a device for magnetic field therapy with improved handling properties. In the same time, it is desired to maintain a treatment volume as large as possible.

Another object of the invention is to provide a device for magnetic field therapy which is easily manufactured and which is suitable for use in therapy forms that are based on the effect of nuclear magnetic resonance due to a good homogeneity of the field.

Moreover, it is an object of the invention to ameliorate the accessibility of the treatment zone for the patients.

Yet another object of the invention is to maintain the treatment zone of a device for magnetic field therapy, with the exception of a couch surface, as open as possible, and accessible from all sides.

SUMMARY OF THE INVENTION

This object of the invention is already achieved by a device for magnetic field therapy according to the independent claim.

Preferred embodiments and modifications of the invention are set forth in the respective dependent claims.

The invention relates to a device for magnetic field therapy, in particular the invention relates to a device which is adapted to achieve nuclear magnetic resonances in the tissue to be treated.

The device comprises a base which is preferably arranged horizontally and is particularly formed as a couch surface for a patient or a body part of a patient.

Furthermore, the device comprises two angled and/or curved side parts which are disposed at the sides of the base and preferably extend in vertical direction from the sides of the base.

Each of the side parts includes a coil having a central axis that extends transversely, preferably substantially perpendicular to the respective side part.

The arrangement of the coils in the side parts allows a construction of the device such that the device opens upwardly.

Moreover, by integrating a pair of coils in the side parts, a magnetic field with fairly good homogeneity can be generated. Since the magnetic field extends substantially linearly from one of the side parts to the other one, quite a large treatment volume may be provided in which nuclear magnetic resonances are achieved. So, the coils are provided as some kind of Helmholtz coil pair.

Preferably, the entire device is approximately U-shaped.

In contrast to known devices for magnetic field therapy that use annular or cylindrical coils, the invention provides accessibility of the treatment zone from above. So the patient do not has to be driven into the coil arrangement but can lie back by his own and can enter the treatment zone in this manner with at least one body part.

When treating animals, the simplified accessibility also provides for a significantly easier treatment. So, e.g., a dog or a small animal can be introduced into the treatment zone from above and can additionally be supervised during treatment and does not have to be strapped down or otherwise fixed on a couch.

Further, the device comprises a first means for generating a magnetic field, wherein the magnetic field generated by this first means is transverse, preferably substantially perpendicular to the field generated by the coils.

By combining a substantially static field with a superimposed alternating field nuclear magnetic resonances can be produced in the tissue to be treated.

In a preferred embodiment of the invention the first means for generating a magnetic field comprises at least one coil which has a substantially flat cross-section and is disposed in or below the base.

In this embodiment, the magnetic field generated by the first magnetic field generating means is not generated by a permanent magnet but also by means of a coil.

Preferably, a flat cylindrical or annular coil laid flat in the base is used.

It will be understood, however, that parts of a coil system even may protrude up and into the side parts.

In one embodiment of the invention, the substantially static magnetic field is generated by the flat lying coil, while the alternating magnetic field substantially perpendicular thereto is generated by the coils integrated in the side parts. In an alternative embodiment in which the alternating field is generated by the first magnetic field generating means, an advantage of the device is the good homogeneity of the field between the side parts.

A combination of permanent magnets and coils for generating the substantially static magnetic field is also contemplated to be within the scope of the invention.

Preferably, the device for magnetic field therapy opens opposite to the base, i.e. in particular upwards, to provide for easier access. The coil systems described can be mounted in a closed casing with or without openings.

In another preferred embodiment the side parts each have a recess, wherein the respective coil extends around the recess.

This embodiment allows a construction in which the side parts substantially only form a frame to receive the coil.

One purpose of the recess is that the treatment zone is not perceived as a narrow tunnel by the patient, as is the case with known annular designs.

On the other hand, light may enter through the recesses so that there will be light also in the treatment zone.

In a modification of the invention a lighting device is provided which is used to mark the treatment zone by a light field.

In a preferred embodiment of the invention, light sources can be switched on as a positioning aid to properly position a patient, preferably by a switch/button arrangement mounted outside. Moreover, it is envisaged to provide for a therapy accompanying light that can be switched on in the treatment zone. Another light means which is for example coupled to at least one other separate coil which is inductively powered through the fields of the means for generating a magnetic field, can be used to indicate the operability of the device for magnetic field therapy.

In a preferred embodiment, the recesses are substantially rectangular. The side parts also have a substantially rectangular shape, as seen in a side view. Such a construction allows providing a substantially rectangular treatment zone with a good use of space.

In a preferred embodiment of the invention, the recesses occupy more than 50%, preferably more than 60% of the area of the side parts.

In a modification of the invention, the side parts are curved within the plane of the coil.

Thus, the coil which is formed as a cylindrical or annular coil and extends within the frame of the side parts is curved along with the side part so providing for a better use of space.

In particular, an approximately circular shape of the side parts is contemplated, as seen in a front view.

The coils preferably used for the various treatment tasks have a diameter from 10 cm to 1 m, more preferably from 50 cm to 90 cm, wherein the base of the device for magnetic field therapy has a length from 20 to 120 cm, preferably from 40 to 80 cm.

The coils in the side parts can be used both for generating a substantially static field and for generating an alternating magnetic field.

In case of use for a static field, the good homogeneity of the field is of particular advantage, since the frequency of the alternating field required to achieve nuclear magnetic resonance depends on the strength of the static field.

But even with a coil laid flat in the base a field of sufficient homogeneity can be produced. In particular, the static field can be swept, which is to generate a field with a sufficient minimum field strength which is varied such that by altering the static field it is ensured that during sweeping the resonance condition is produced in every portion of the treatment zone, at least for a short time.

A similar result may be obtained by sweeping the frequency of the alternating magnetic field.

The base and side parts with the respective coils are preferably formed as a unitary module, particularly formed from a plastic material. For example, in a particularly simple way the coils can be integrated in an injection molded casing, and especially can be coated with a plastic material, plastic foam or another dielectric material in an injection mold.

In a modification of the invention, the device for magnetic field therapy additionally comprises a carriage which is disposed on the base and includes a couch surface, and which can be displaced relative to the base. Thus, by translating the carriage it is possible to move the treatment zone relative to the patient and to treat several portions of the body.

In an alternative embodiment of the invention, a module formed by the base and the side parts is constructed to be movable relative to the level of a seat. In this embodiment of the invention, the base is arranged substantially vertically and can be moved upwards and downwards along the body of the patient who sits on the seat. This embodiment of the invention is especially suitable for a treatment in the head or upper body zone. It is particularly useful for skin treatment in the facial area.

In a modification of the invention, the module is adapted to be pivotable and so can be tilted from an exactly vertical position to be optimally adjustable in function of the seating position and the zone of the body to be treated.

BRIEF DESCRIPTION OF THE DRAWINGS

The invention will now be described in detail with reference to exemplary embodiments schematically illustrated in the drawings of FIGS. 1 to 5.

DETAILED DESCRIPTION OF THE DRAWINGS

Figure 1:
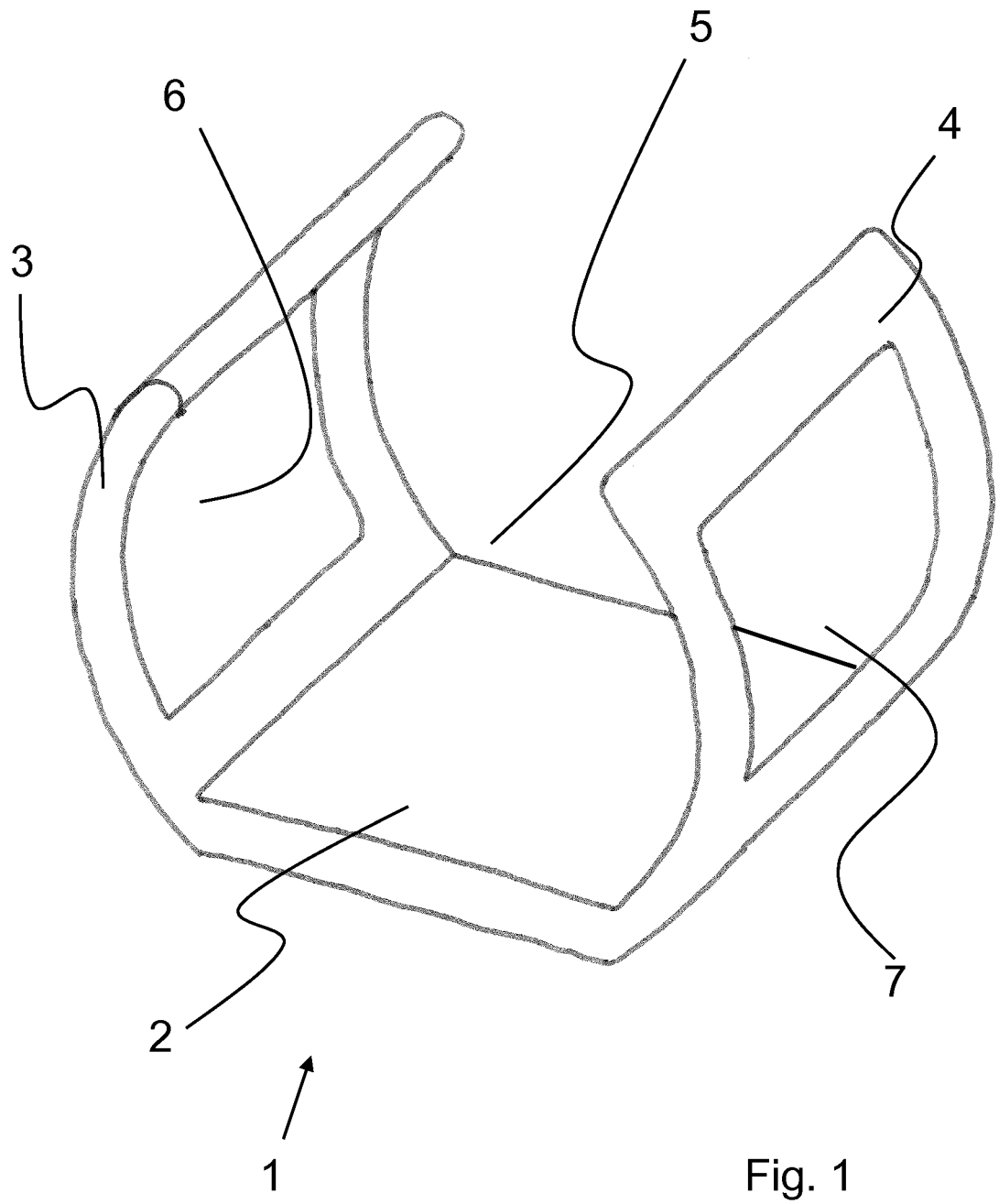
FIG. 1 schematically shows a perspective view of an exemplary embodiment of the invention.

FIG. 1 schematically illustrates a device 1 for magnetic field therapy.

Device 1 for magnetic field therapy comprises a base 2, which for example serves as a rest for a body part to be treated.

Two side parts 3 and 4 extend from base 2.

Side parts 3 and 4 have a curved shape, as seen in a front view, and have an approximately circular segment shaped or U-shaped cross-section.

Furthermore, the two side parts 3 and 4 form a frame and so each have a recess 6, 7.

Device 1 for magnetic field therapy is open opposite base 2 thereby providing for significantly better accessibility of the treatment zone 5 provided between side parts 3, 4 and base 2, as compared to known devices for magnetic field therapy.

A first means for generating an magnetic field (not shown) is provided in base 2.

Figure 2:
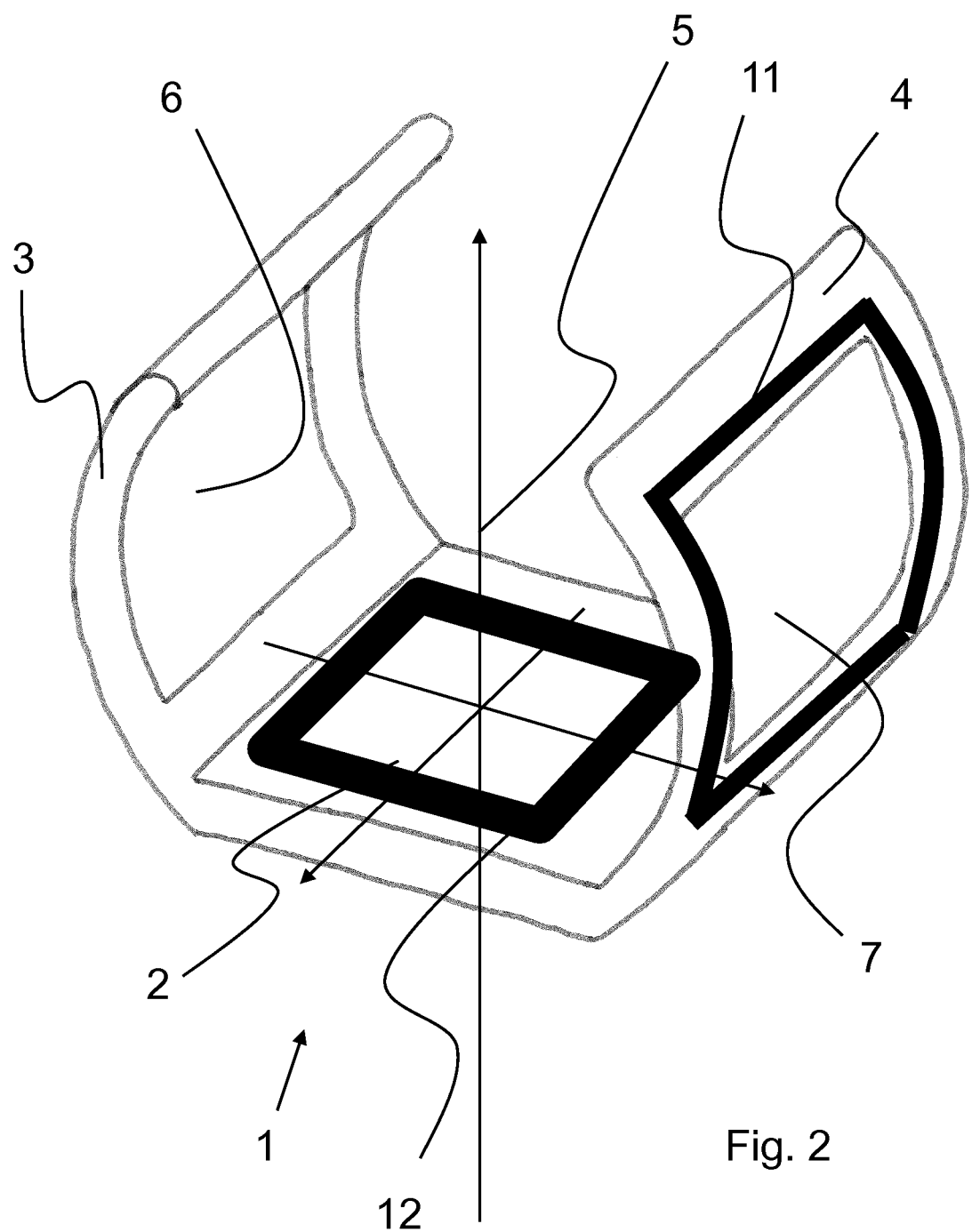
FIG. 2 shows the exemplary embodiment illustrated in FIG. 1, the arrangement of coils being schematically illustrated.

FIG. 2 shows the embodiment of a device 1 for magnetic field therapy according to FIG. 1, this view schematically showing a coil 12 integrated in base 2 which provides a first means for generating a magnetic field.

Another coil 11 is provided in the right-hand side part 4 which can also be used to produce a magnetic field.

The coil in side part 3 is not shown, but it can be seen that a magnetic field can be generated by means of the coils in side part 3 and side part 4 which is substantially perpendicular to the magnetic field generated by coil 12.

Coils 11, 12 can be powered via a control device that is independent from a power supply system, in particular a device that includes an accumulator (not shown).

In this manner, nuclear magnetic resonances can be generated in the skin area to be treated (not shown) within the treatment zone 5.

Through recesses 6 and 7, the treatment zone 5 can be marked using a light (not shown).

Figure 3:
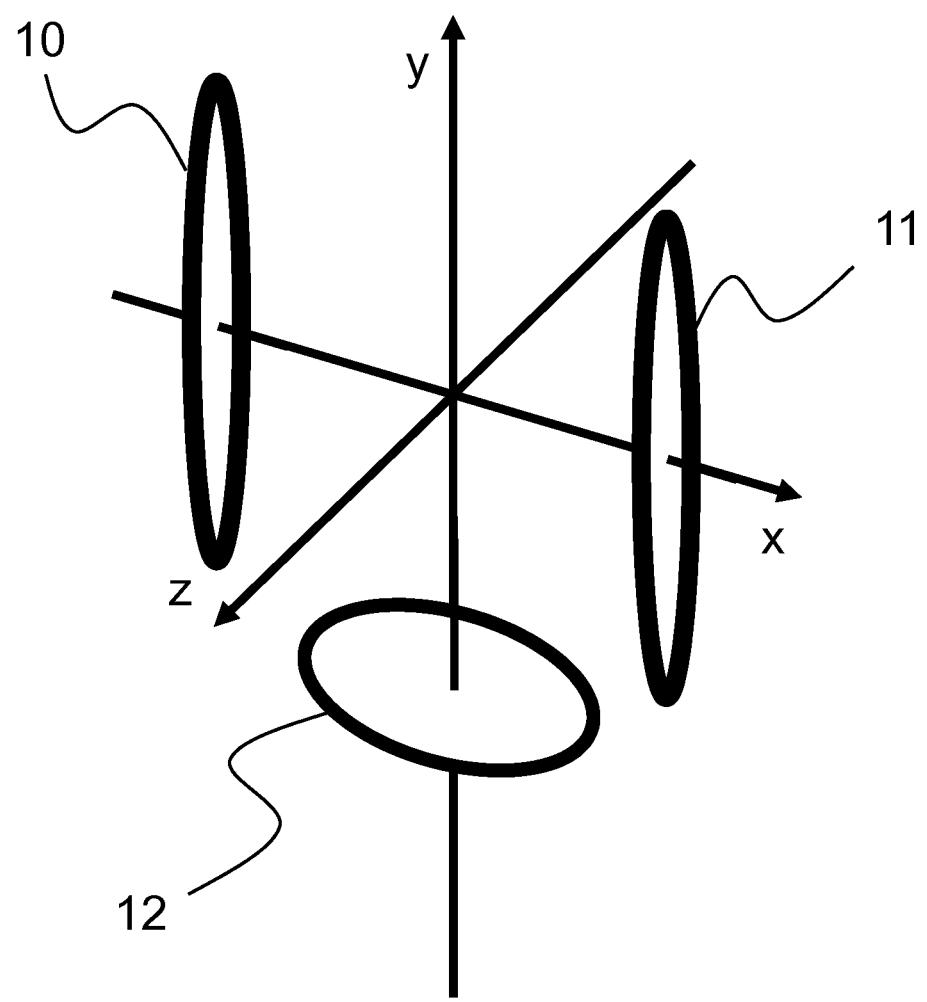
FIG. 3 schematically shows the arrangement of coils.

FIG. 3 schematically illustrates the coil arrangement.

A first magnetic field is produced by coil 12 incorporated in the base, with field lines that substantially extend along the y-axis within the treatment zone.

Coils 10 and 11 are used to produce a field perpendicular thereto which has field lines that extend substantially along the x-axis. Thus, coils 10 and 11 form a second means for generating a magnetic field.

The field generated by coils 10 and 11 is very homogeneous, due to the arrangement being very similar to a Helmholtz coil. Thus, for producing nuclear magnetic resonances in the tissue to be treated it is advantageous to produce a substantially static magnetic field using coils 10 and 11, and to produce an alternating field perpendicular thereto using coil 12 which results in the spins folding down.

Figure 4:
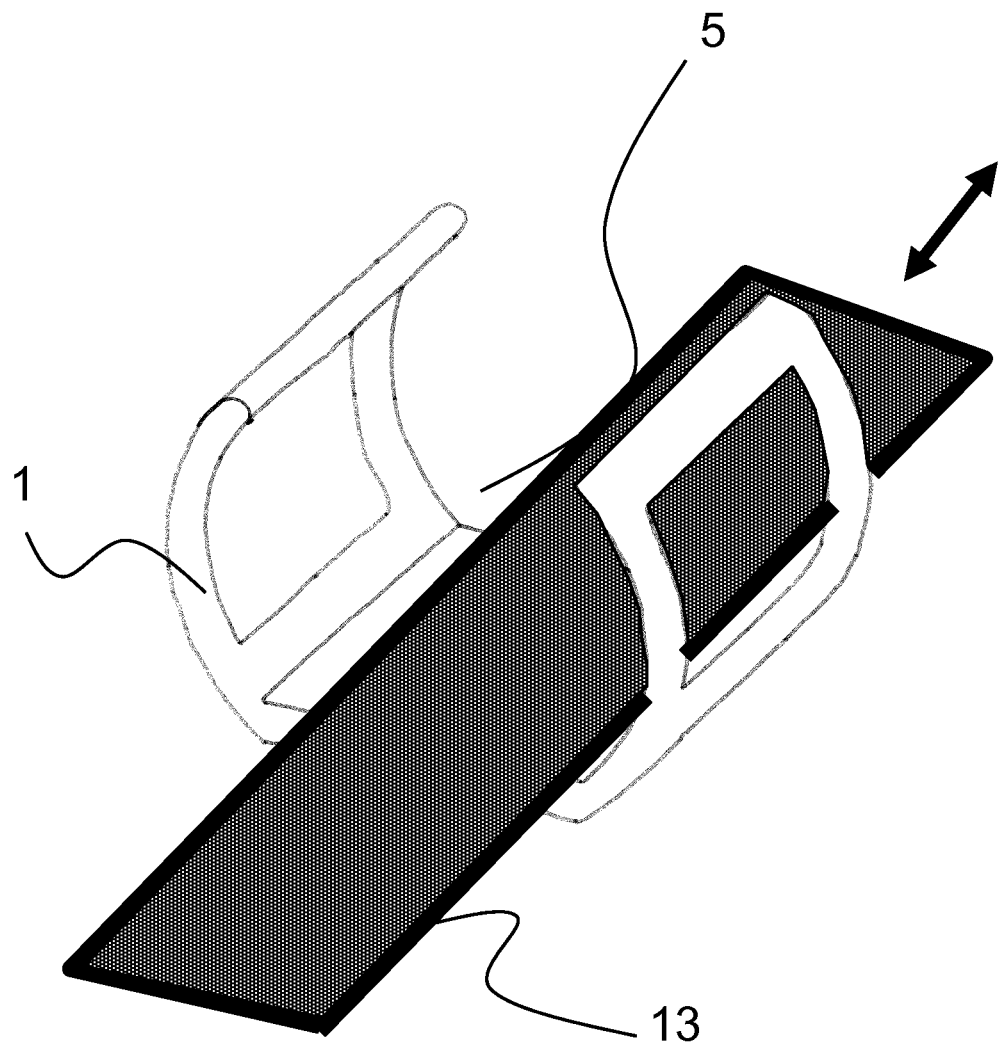
FIG. 4 shows another exemplary embodiment of a device for magnetic field therapy that includes an adjustable couch.

FIG. 4 schematically illustrates another embodiment of the invention. In this embodiment, the device 1 for magnetic field therapy illustrated in FIG. 1 and FIG. 2 is equipped with a couch moveable along the base of the device. By moving couch 13 relative to the device 1 for magnetic field therapy, the treatment zone 5 may be slightly displaced, if a patient lies on the couch (not shown), and in this way several zones of the body may be treated successively.

Figure 5:
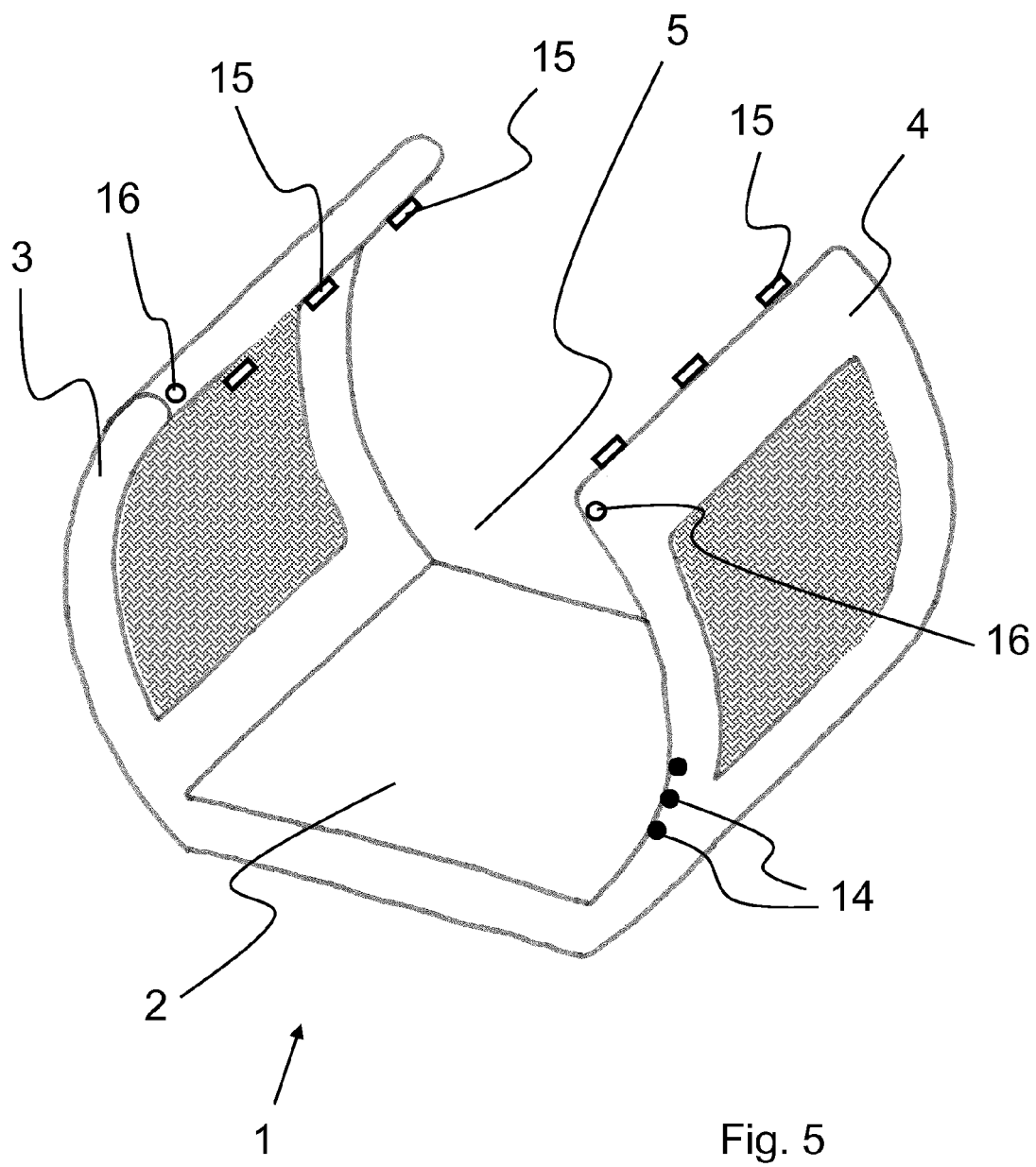
FIG. 5 shows another exemplary embodiment of the invention.

Referring to FIG. 5 another exemplary embodiment of the invention will be described in detail.

The figure likewise illustrates a device 1 for magnetic field therapy, wherein in this exemplary embodiment side parts 3, 4 do not have any recesses, rather they are closed. Otherwise, the basic form of the device 1 for magnetic field therapy corresponds to that of the device illustrated in FIG. 1.

Additionally, an arrangement of switches 14 is illustrated in the drawing which can be used for example to operate the device or to switch on and off lights 15. Lights 15 are preferably provided as LED lights. In this exemplary embodiment three lights are provided on each side to mark the treatment zone 5.

Furthermore, the device 1 for magnetic field therapy comprises operation indicators 16 from which it can be seen if the device works. Operation indicators 16 may e.g. comprise an LED which is connected to another coil (not shown), wherein in case of correct operation the LED is inductively powered through the coil.

Figure 6:
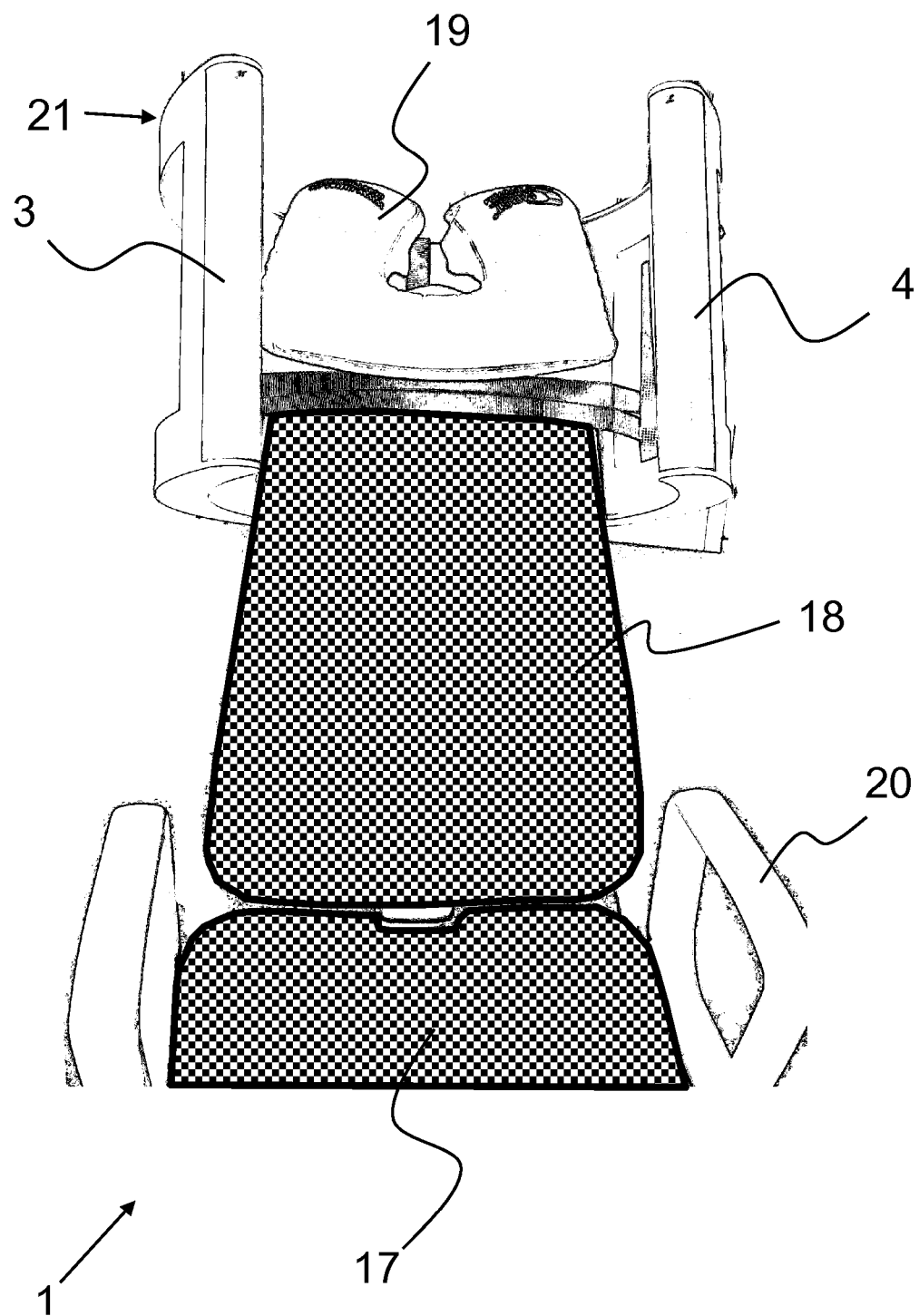
FIG. 6 shows another exemplary embodiment of the invention in which a seat is provided.

FIG. 6 shows an alternative embodiment of the invention in which the device 1 for magnetic field therapy comprises a seat 17 on which the patient may sit down. For enhancing comfort, the device additionally comprises a backrest 18, an armrest 20, and a neck cushion 19.

A module 21, which comprises a base and side parts 3, 4 is disposed substantially vertically.

Module 21 is preferably adjustable, at least in height, so that the device 1 for magnetic field therapy can be adjusted to different sizes of patients or to treat different skin portions.

It will be understood that the invention is not limited to a combination of features described above, rather a person skilled in the art will combine any features as far as appropriate.

LIST OF REFERENCE NUMERALS 1 device for magnetic field therapy
2 base
3 side part
4 side part
5 treatment zone
6 recess
7 recess
10 coil
11 coil
12 coil
13 couch
14 switch
15 light
16 operation indicator
17 seat
18 backrest
19 cushion
20 armrest
21 module

The invention claimed is:

1. A device for magnetic field therapy, comprising:
a base with a first device generating an alternating first magnetic field, wherein the base comprises a couch surface for a patient, a first angled side part and a second angled side part, wherein the first angled side part and the second angled side part, each extend vertically from respective first opposed sides of the base;
wherein the first angled side part includes a first coil and the second angled side part includes a second coil, each of the first and second coils comprising a central axis that extends perpendicular to the respective first and second angled side part; and
a control device for powering the first and second coils generating a substantially static second magnetic field which extends substantially linearly from the first angled side part to the second angled side part;
wherein the substantially static second magnetic field produced by said coils is perpendicular to the magnetic field produced by said first device generating the alternating first magnetic field, at least in portions thereof, and wherein the device for magnetic field therapy is open opposite to the base, and wherein the device for magnetic field therapy is open at second opposed sides of the base, the device opening upwardly such that a patient or animal to be treated can enter a treatment zone between the first angled side part and the second angled side part from above the base;
wherein the couch surface extends beyond the base; and
wherein said first angled side part and second angled side part each has a curved shape as seen in a front view and wherein said device for magnetic field therapy is approximately U-shaped.

2. The device of claim 1, wherein the first device generating the magnetic field comprises at least a third coil arranged in or below the base and having a substantially flat cross-section.

3. The device of claim 1, wherein the first device generating the magnetic field comprises a third coil having a central axis that extends substantially perpendicular to the base.

4. The device of claim 1, wherein the first and second angled side parts each have a recess.

5. The device of claim 4, wherein the recesses have a rectangular shape.

6. The device of claim 4, wherein each angled side part has an area and each recess occupies about 50% or more of the area of the respective side part.

7. The device of claim 1, wherein the first and second angled side parts are of a frame-type construction.

8. The device of claim 1, wherein the coils have a diameter from about 10 cm to about 1 m.

9. The device of claim 1, wherein the base has a length from about 20 to about 120 cm.

10. The device of claim 1, wherein the base with the first device generating the magnetic field and the first and second angled side parts with the coils are formed as a unitary module.

11. The device of claim 1, wherein the base and the first and second angled side parts comprise a dielectric material.

12. The device of claim 1, further comprising a carriage arranged on the base and comprising the couch surface, wherein said carriage is adapted to be moveable relative to the base.

13. The device of claim 1, wherein the base is arranged horizontally.

14. The device of claim 1, comprising:
   a seat having a level; and
   a module formed by said base and said first and second angled side parts which is displaceable relative to the level of the seat.

\* \* \* \* \*